United States Patent [19]

Bille

[11] Patent Number: 4,988,348

[45] Date of Patent: Jan. 29, 1991

[54] METHOD FOR RESHAPING THE CORNEA

[75] Inventor: Josef F. Bille, Rancho Santa Fe, Calif.

[73] Assignee: Intelligent Surgical Lasers, Inc., San Diego, Calif.

[21] Appl. No.: 357,705

[22] Filed: May 26, 1989

[51] Int. Cl.⁵ ............................................. A61N 5/06
[52] U.S. Cl. ...................................... 606/5; 128/395; 128/898
[58] Field of Search ................ 128/395, 397, 398, 897, 128/898; 606/3-5, 10, 11-13, 16-19, 66

[56] References Cited

U.S. PATENT DOCUMENTS

| | | | |
|---|---|---|---|
| 4,669,466 | 6/1987 | L'Esperance | 606/5 |
| 4,729,372 | 3/1988 | L'Esperance, Jr. | 606/5 |
| 4,732,148 | 3/1988 | L'Esperance, Jr. | 128/303 |
| 4,770,172 | 9/1988 | L'Esperance, Jr. | 128/303 |
| 4,773,414 | 9/1988 | L'Esperance, Jr. | 128/303 |
| 4,887,592 | 12/1989 | Loertaeher | 128/395 |

OTHER PUBLICATIONS

"Enodexcimer Laser Intraocular Ablative Photodecomposition", by Marshall et al. Am. J. Apthal. 1/86, vol. 101, No. 1, pp. 130-131.

"Photoablative Reprofiling of the Cornea Using an Excimer Laser: Photorefractive Keratechtomy", Marshall et al.; Lasers in Ophthal., vol. 1, No. 1, pp. 21-48 (1986).

Primary Examiner—Lee S. Cohen
Assistant Examiner—David Shay
Attorney, Agent, or Firm—Neil K. Nydegger

[57] ABSTRACT

A method for reshaping the cornea comprises an initial step of determining the precise volume of corneal tissue which must be removed in order to attain the desired vision correction. A pulses laser beam, having a pulse energy density sufficient to cause photoablation of corneal tissue near the threshold of the plasma regime, is directed onto the eye for removal of relatively large portions of tissue from the precisely determined volume to establish a corrected surface. A pulsed laser beam, having a pulse energy density sufficient to cause photoablation of corneal tissue substantially below the threshold of the plasma regime, is then directed onto the corrected surface to take away relatively small portions of corneal tissue and thereby smooth the corrected surface.

25 Claims, 2 Drawing Sheets

METHOD FOR RESHAPING THE CORNEA

FIELD OF THE INVENTION

The present invention pertains to ophthalmic surgical procedures for reshaping the cornea of the eye in order to correct vision deficiencies. More particularly, the present invention pertains to ophthalmic surgical procedures which incorporate use of a pulsed laser beam for the photoablation and removal of corneal tissue. The present invention is particularly, but not exclusively, useful for reshaping the cornea to attain the desired vision correction by photoablating a predetermined volume of corneal tissue.

BACKGROUND OF THE INVENTION

It is well known that defective vision can be corrected by reshaping the cornea of the eye. Further, it is known that reshaping of the cornea can be accomplished in several ways. For example, the well known radial keratotomy procedure is used to establish weakened areas in the cornea which respond to internal pressure in the eye to move the cornea in its optical relationship with the retina. Another way in which vision can be corrected is by procedures which actually remove portions of the cornea to alter its optical properties. For the category of procedures wherein portions of the cornea are removed in order to directly alter its optical properties, there is an increased appreciation that lasers may be efficacious as a surgical tool. U.S. Pat. No. 4,732,148 and U.S. Pat. No. 4,773,414 which issued to L'Esperance Jr. for inventions entitled "Methods for Performing Ophthalmic Laser Surgery" and "Method of Laser-Sculpture of the Optically Used Portion of the Cornea", respectively, are both exemplary of efforts to use laser beams for ophthalmic surgery on the cornea. These procedures, however, require there be some initial mechanical removal of portions of the cornea as preparation for the subsequent removal of corneal tissue by photoablation. As will be readily appreciated by the skilled artisan, such a requirement necessitates the use of different surgical tools in the same operation. It is, of course, preferable if the same surgical tool can be used throughout the procedure. The present invention recognizes that a laser beam can be such a tool for the purpose of ophthalmic surgery which reshapes the cornea. In order to be effective as a surgical tool, however, laser beams must be precisely controlled. Thus, their operative characteristics must be carefully selected and these characteristics must be variable to meet the particular needs of the particular procedure.

In light of the above, it is an object of the present invention to provide a method for reshaping the cornea of the eye in which the pulse energy density or the wavelength of a pulsed laser beam can be varied to precisely control the photoablation of corneal tissue. Another object of the present invention is to provide a method for reshaping the cornea of the eye in which the removal of a precisely predetermined volume of corneal tissue is accomplished by a two-stage photoablation procedure that first takes away relatively large portions of corneal tissue and subsequently takes away relatively small portions of corneal tissue. Still another object of the present invention is to provide a method for reshaping the cornea of the eye using a pulsed laser beam in which the pulse energy density is relatively low. Yet another object of the present invention is to provide a method for reshaping the cornea of the eye which minimizes or avoids the adverse side effects caused when photoablation of corneal tissue is accomplished using a pulsed laser beam with pulse energy densities in the plasma regime. Another object of the present invention is to provide a method for reshaping the cornea of the eye which does not involve or require the mechanical removal of corneal tissue. Still another object of the present invention is to provide a method for reshaping the cornea of the eye which is an essentially continuous operation. Yet another object of the present invention is to provide a method for reshaping the cornea of the eye which is simple to accomplish and which is relatively cost effective.

SUMMARY OF THE INVENTION

The present invention pertains to a method for reshaping the cornea of an eye using photoablation techniques. More specifically, in accordance with the present invention, the methods for reshaping the cornea employ lasers which can be controllably varied in wavelength, pulse energy density and focused spot size to effectively photoablate the various tissues in the stroma which require removal.

Using well known techniques, the precise volume of corneal tissue which must be removed in order to attain the desired vision correction can be predetermined. One such technique assumes that a one (1) diopter correction will be realized by the removal of corneal tissue which corresponds to an extent of approximately eight (8) microns in depth along the eye's visual axis. In order to do this, the methods of the present invention contemplate removal of tissue by photoablation from the epithelium, Bowman's membrane and the stroma. Further, the present invention contemplates this photoablation can be accomplished in two stages. First, there is the removal or grinding of relatively large portions of tissue from the predetermined volume to establish a corrected surface. This is done through the photoablation of tissue by pulses of laser energy able to remove portions of tissue which are approximately one hundred (100) microns in diameter and in the range of one to eight (1-8) microns in depth. Preferably, in this first stage, a pulsed laser beam is used that has a pulse energy density which will cause photoablation near the threshold of the plasma regime of the corneal tissue being removed. Next, there is the smoothing or polishing of the corrected surface in which the photoablation of tissue is accomplished by pulses of laser energy which remove portions of tissue that are approximately one (1) micron in diameter and on the order of one (1) micron in depth. For this subsequent stage, a pulsed laser beam is used which has a pulse energy density that is substantially below the threshold of the plasma regime but which will still cause photoablation of corneal tissue.

According to one procedural operation, as contemplated by the present invention, each stage of the procedure is accomplished using pulsed laser beams of different wavelengths. During the removal or grinding stage the wavelength of the laser is selected according to its efficacy for removing the particular tissue. Generally, it is preferred that a 0.527 micron wavelength (green) laser which is generated by a Nd:YLF crystal be used in this stage for the relatively rapid removal of selected portions of epithelial tissue, Bowman's membrane, and stroma. This removal or grinding stage is continued until substantially all of the predetermined volume of corneal tissue is removed and a corrected surface is exposed. Once the predetermined volume has been removed, the corrected surface which has been exposed is then smoothed or polished. This so-called second stage is accomplished by scanning the entire corrected surface with a laser generated by an erbium crystal having the longer 2.94 micron wavelength.

Alternatively, tissue removal and tissue smoothing can be accomplished using a single crystal and, hence, a single wavelength. For example, in addition to effectively removing relatively large portions of corneal tissue to expose the corrected surface, the pulsed beam generated by a Nd:YLF crystal may also be used to smooth the corrected surface. Smoothing this surface with the Nd:YLF, however, requires additional elements in the beam generator which are able to compress the pulses. Addition of these elements may be undesirable. Similarly, a pulsed laser beam generated by an erbium crystal can be used both for removing corneal tissue to expose a corrected surface and for smoothing this surface. However, in order to generate a pulse energy density for this beam which is sufficient to remove relatively large portions of corneal tissue within a realistic time period, it is necessary to improve the efficiency of the erbium laser. This increase in efficiency can be accomplished in several ways, perhaps most typically by including equipment which will refrigerate or cool the erbium crystal. Again, the addition of elements may be undesirable.

As a final step, and regardless whether a single or dual crystal procedure is used, the smoothed or polished surface can be sealed. For example, the corrected surface may be heat treated by semiliquification after it has been smoothed. Further, it may be possible to chemically treat and seal the corrected surface after the cornea has been reshaped.

The novel features of this invention, as well as the invention itself, both as to its structure and its operation, will be best understood from the accompanying drawings, taken in conjunction with the accompanying description, in which similar reference characters refer to similar parts, and in which:

DESCRIPTION OF THE PREFERRED METHOD

Figure 1:
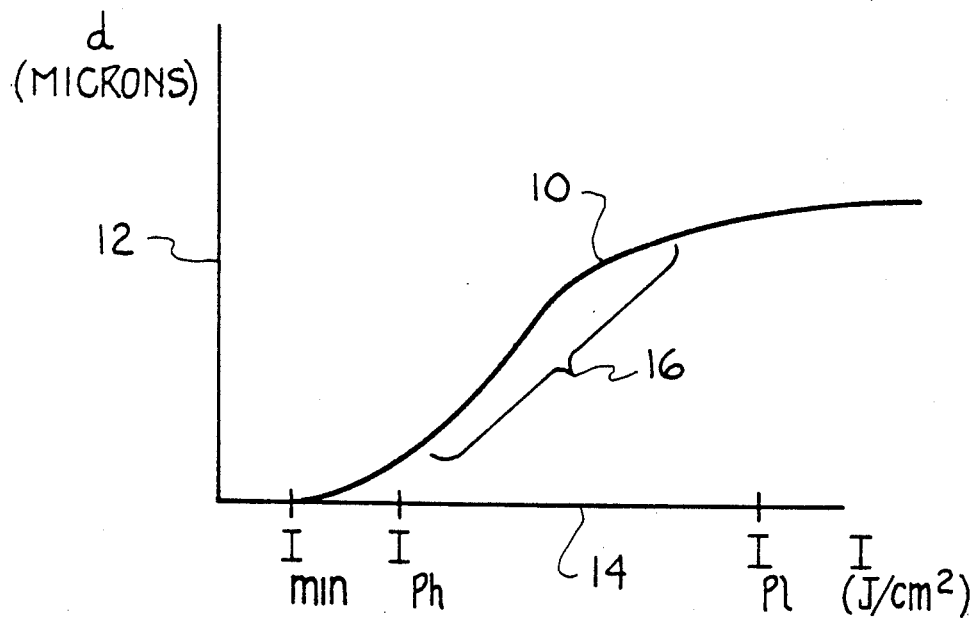
FIG. 1 is a theoretical curve relating tissue ablation depth to the pulse energy density of a pulsed laser beam.

Before considering a specific application for the photoablation of living tissue, it is first helpful to appreciate and understand some general notions about the reaction of living tissue to the photoablation process. For this purpose FIG. 1 shows a curve 10 which indicates the theoretical relationship between the pulse energy density (I) of the laser beam and the resultant ablation depth (d) into the tissue. Specifically, ablation depth (d) (measured in microns) is indicated along ordinate 12 and the pulse energy density (measured in joules per square centimeter) is indicated along abscissa 14. As shown, curve 10 identifies several points and regions of particular interest. For instance, there is some initial pulse energy density ($I_{min}$) which is required before the pulsed laser beam has any affect on the tissue. Theoretically, $I_{min}$ will be approximately one (1.0) J/cm². At a slightly higher pulse energy density designated $I_{ph}$, tissue begins to photoablate. As shown on curve 10 photoablation begins to occur when $I_{ph}$ is equal to approximately one and one half (1.5) J/cm². FIG. 1 also indicates there is a substantially linear region 16 on curve 10 which extends from $I_{ph}$ through higher pulse energy densities until the photoablation process begins to create a plasma at $I_{pl}$. At pulse energy densities above $I_{pl}$ it is generally accepted that curve 10 will begin to flatten out in accordance with a logarithmic relationship. The focus of the present invention, however, is not on elevated pulse energy densities. Indeed, such elevated energy pulse densities should be avoided in order to minimize the adverse side effects caused by the formation of plasma, i.e., heat and mechanical shock. Rather, the present invention is concerned with the resultant ablation depth of tissue for pulse energy densities which are substantially between $I_{ph}$ and a value slightly greater than $I_{pl}$. Importantly, there is a general linear relationship between ablation depth and the pulse energy density I for values of I in this range.

Figure 2:
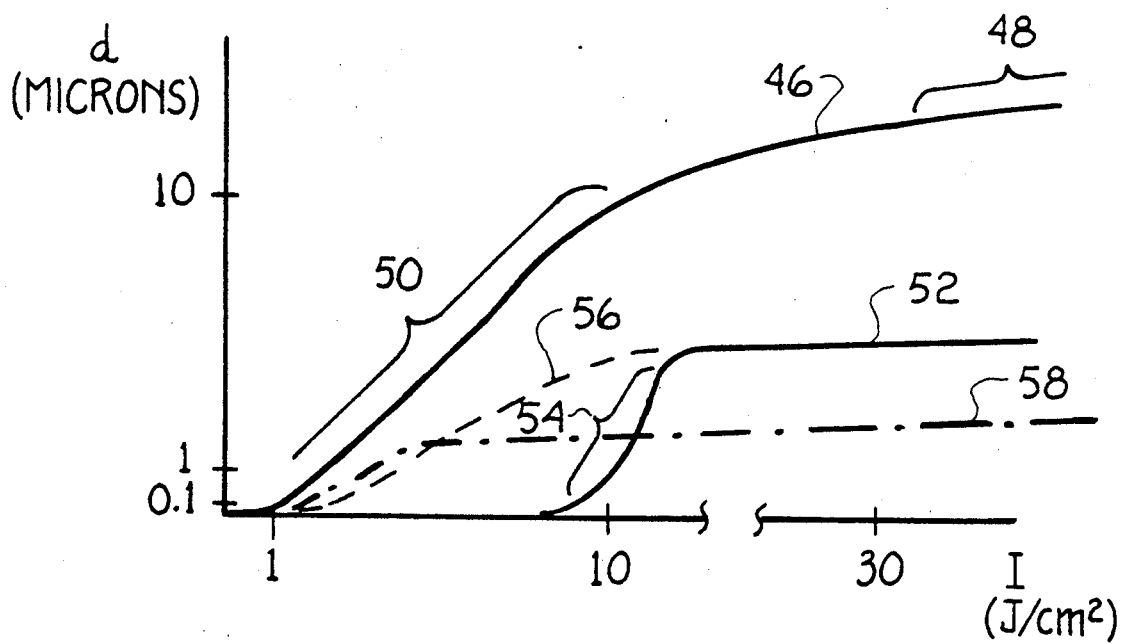
FIG. 2 is an empirical curve relating tissue ablation depth to pulse energy densities for various pulsed laser beams of selected wavelength.

As should be expected, it is necessary to also consider the wavelength of the particular laser beam that is to be used for the photoablation of living tissue. For this purpose, FIG. 2 shows several ablation curves which generally indicate the respective causal relationships between ablation depth (d) and pulse energy density (I) for several laser beams of differing wavelengths. Although it is recognized that other laser mediums which are well known to the skilled artisan can be used to generate pulsed laser beams that may also be effective for the purposes of the present invention, the consideration here will be on only two such mediums. Specifically, the present invention is concerned with the well known Nd:YLF laser crystal which emits laser light with a wavelength of approximately 0.527 microns. Also, the present invention is concerned with the well known erbium laser crystal which generates laser light at a wavelength of 2.94 microns. Both mediums have certain beneficial characteristics.

Simply stated, the general objectives of the method and procedure according to the present invention are to remove a predetermined volume of corneal tissue which will effectively reshape the cornea in order to obtain a desired vision correction. To accomplish this it is necessary to first determine the volume of corneal tissue which must be removed. Several methods for determining this volume are well known in the pertinent art and all of these methods need not be disclosed here in detail. One in particular, however, helps to more fully understand the method of the present invention. According to this particular calculation, it is known that removal of an eight (8) micron thick layer of stroma tissue along the visual axis will result in an approximately one (1) diopter correction for the eye. To more fully appreciate what this means, consider FIG. 3.

Figure 3:
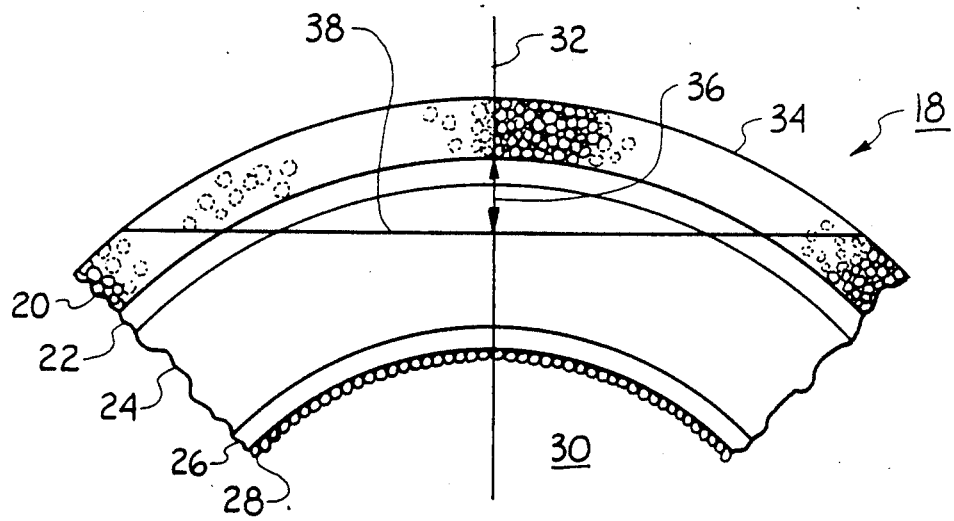
FIG. 3 is a cross-sectional view of the cornea of the eye.
Figure 4:
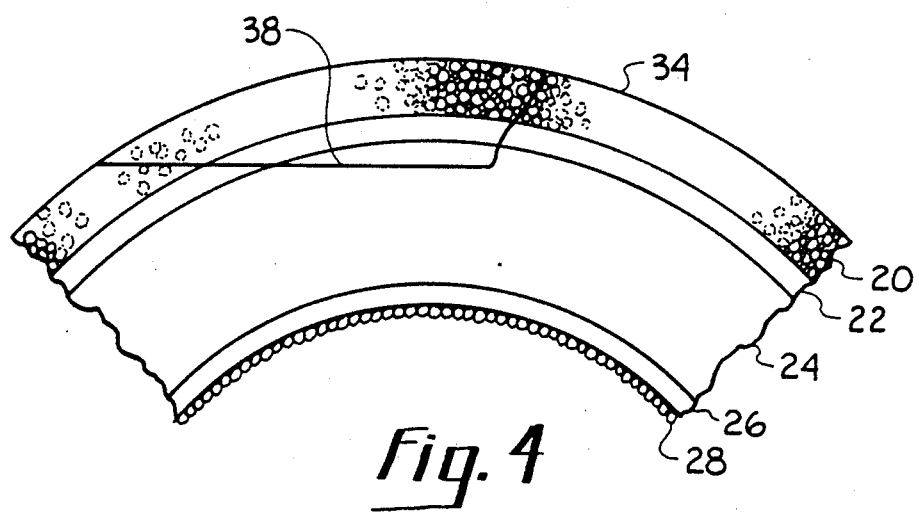
FIG. 4 is a cross-sectional view of the cornea shown in FIG. 3 with portions of a predetermined volume of corneal tissue removed by photoablation.

FIG. 3 depicts a cross section of the cornea of an eye, generally designated 18. As shown, cornea 18 comprises an epithelium 20, Bowman's membrane 22, stroma 24, Decimet's membrane 26, and an endothelium 28. Behind the cornea 18, and inside the eye, is the aqueous humor 30. The eye's visual axis 32 is shown in FIG. 3 as being along a line which extends in the direction of sight and which is substantially normal to the external surface 34 of cornea 18. As indicated above, certain vision deficiencies may be corrected by removal of tissue from stroma 24. Specifically, the amount of correction will depend on how much tissue is removed and from where. More specifically, it is known that a distance 36 measured along visual axis 32 in stroma 24 can be used to calculate the amount of tissue to be removed for a desired diopter correction. Thus, for approximately each eight (8) microns of distance 36, a one (1) diopter correction will result. To realize such a correction, however, it is necessary to remove a predetermined volume of corneal tissue approximately equal to a dome having a radius of curvature substantially equivalent to that of cornea 18 and a height equal to the sum of distance 36, the depth of epithelium 20 and Bowman's membrane 22. It is to be appreciated that this is but one of several possible solutions to the problem. The exact predetermined volume of tissue to be removed is a matter of choice which can be determined on a case-by-case basis without consequence to the remainder of the procedure. In any event, the result after removal of the predetemined volume of corneal tissue is the exposure of a corrected surface 38.

Figure 5:
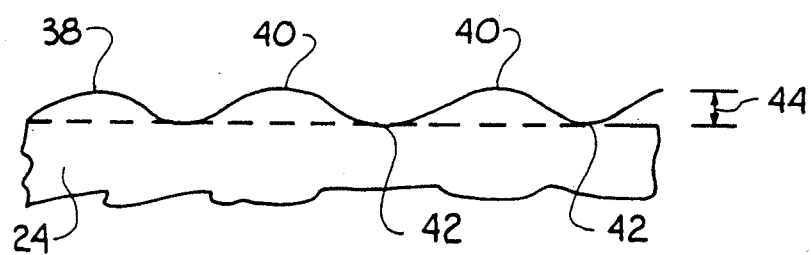
FIG. 5 is an enlarged cross-sectional view of a portion of the corrected surface shown in FIG. 4.

As contemplated by the present invention, reshaping of the cornea is accomplished by a two-stage photoablation procedure. After the volume of corneal tissue to be removed has been determined, relatively large portions of this volume are removed in the first stage by photoablation. Ideally, portions of tissue in the size of up to one thousand (1,000) cubic microns are removed during this stage with each pulse of the laser beam. This removal or grinding step can be controlled by a device, such as the one disclosed in U.S. Pat. No. 4,901,718 for an invention entitled "3-Dimensional Laser Beam Guidance System," filed Feb. 2, 1988, which issued on Feb. 20, 1990 is assigned to the same assignee as the present invention. After this removal of tissue, however, the corrected surface 38 of the reshaped cornea 18 remains somewhat uneven and irregular. Specifically, corrected surface 38 is characterized by ridges 40 and depressions 42, as generally shown in FIG. 5. It is expected that the elevational difference 44 between a ridge 40 and a depression 42 will be on the order of one (1) or two (2) microns. This difference 44 can, however, cause hazy vision and in order to avoid hazy, albeit corrected, vision for the patient corrected surface 38 needs to be smoothed or polished.

In the second stage of this procedure, corrected surface 38 is smoothed or polished by removing relatively small portions of corneal tissue by photoablation. Ideally, only the ridges 40 are removed and therefore, during this smoothing stage, it is necessary to use laser pulses which photoablate stroma 24 tissue to a depth of one (1) micron or less. Ideally, as envisioned by the present invention, the depth of photoablation in the smoothing stage will be variable within the range of one (1) to one tenth (0.1) micron.

Referring to FIG. 5, it can be appreciated that only selected portions of corrected surface 38 should be photoablated during the smoothing stage. Specifically, it is desired to remove only the ridges 40. To do so, however, requires determining the precise location of the ridges 40. Preferably, the determination of where ridges 40 are located on corrected surface 38 is done by using a device such as the one disclosed in U.S. Pat. No. 4,881,808 for an invention entitled "Imaging System for Surgical Lasers," filed Feb. 10, 1988, which issued Nov. 21, 1989, and is assigned to the same assignee as the present invention and which is incorporated here by reference. Briefly, this device is able to establish the topography of corrected surface 38 by calculating reception responses of specular reflections from the corrected surface 38. With this information, the location of ridges 40 can be ascertained and they can then be removed by directing a pulsed laser beam of specific characteristics directly into the ridge 40.

As mentioned above, it is to be appreciated that lasers with different wavelengths may be used for the present invention. Ideally, one wavelength could be used for both the first stage (i.e., removal of relatively large portions of corneal tissue) and the second stage (i.e., smoothing of the corrected surface by removal of relatively small portions of corneal tissue). This may, however, be impractical. Nevertheless, the use of single wavelength procedures should be considered along with the presently preferred dual wavelength procedure.

Consider first, the use of only an erbium (Er) laser crystal. As is well known, an erbium crystal emits laser light at a wavelength of approximately 2.94 microns. Further, it has been determined that the light emitted by an erbium laser crystal has photoablation characteristics which are generally as depicted by curve 46 in FIG. 2. Specifically, as with other pulsed laser beams, there is a region which extends from a pulse energy density of approximately thirty (30) J/cm$^2$ upward to higher pulse energy densities in which operation of an erbium pulsed laser beam will cause formation of a plasma during photoablation. Importantly, however, the erbium laser also has characteristics in range 50 of pulse energy densities below approximately ten (10) J/cm$^2$ wherein photoablation will result without any significant formation of a plasma. Equally important are the indications that the shape of curve 46 in the range 50 is moderate and the curve 46 itself is substantially linear. Consequently, an erbium pulsed laser beam lends itself to being precisely controlled during operation in the range 50. Unfortunately, an erbium laser medium has relatively low efficiencies and generates a great amount of heat during operation at pulse energy densities above approximately ten (10) J/cm$^2$. Consequently, in order for an erbium laser to be efficient and have greater efficacy at the higher pulse energy densities necessary for the removal of relatively large portions of corneal tissue in the first stage of the process of the present invention, the erbium medium must be cooled. Further, it is known that this requires cooling the erbium laser medium to approximately minus fifty degrees centigrade ($-50°$ C.) Thus, an erbium laser medium can be used for performing the methods of the present invention if the components necessary to cool the medium to these temperatures in the first stage are provided. On the other hand, for the purposes of the present invention, an Nd:YLF laser medium exhibits good operating characteristics at the higher pulse energy densities required for removal of corneal tissue during the first stage.

As shown in FIG. 2, a standard Nd:YLF laser medium emits light at a wavelength of approximately 0.527 microns in a pulsed beam which has photoablation characteristics that are substantially as depicted by curve 52. Importantly, unlike erbium, an Nd:YLF laser medium does not require cooling for operating the higher pulse energy densities required for efficient removal of relatively large portions of corneal tissue. Thus an Nd:YLF laser beam is preferred for operation during the first stage removal of corneal tissue. An unmodified Nd:YLF laser, however, has less desirable operating characteristics at the lower pulse energy densities. Specifically, as shown in FIG. 2, the shape of curve 52 is relatively steep in region 54 where operation of the Nd:YLF laser would result in removal of relatively small portions of corneal tissue. Thus, it would be difficult to control the Nd:YLF medium in the second stage of the process of the present invention. Perhaps more importantly, it happens at pulse energy densities below approximately ten (10) J/cm², the beam characteristics become somewhat similar to the characteristics of an erbium laser beam if pulses from the Nd:YLF laser medium are compressed. To realize this correlation it is necessary to compress the laser pulses from their relatively easily attained duration of approximately thirty pico seconds (30 psec) down to a duration of approximately one pico second (1 psec).

This relationship is shown in FIG. 2 by curve extension 56. Importantly, compression of the pulses in an Nd:YLF laser beam results in effective operation at the lower energy levels below the level where photoablation results in the formation of a plasma. This results when using compressed pulses due to the more efficient multiple photon absorption processes within the tissue molecules and a coherent cumulative effect of the photons on the particular molecule. Thus, with the incorporation of components in a Nd:YLF laser beam generator which will compress the laser pulses to durations of approximately one pico second (1 psec) at lower pulse energy densities, a Nd:YLF laser could be effectively used for both first and second stage operation of the present invention. Further it is important to note that a system incorporating an Nd:YLF laser medium would lend itself to operations requiring photoablation internally in the eye, such as might be required for retinal surgery.

The photoablation curve 58 for the well known excimer laser is provided in FIG. 2 for comparison purposes only. As clearly seen in FIGS. 1 and 2, the fact that the excimer laser has little, if any, ability to operate at pulse energy densities in region 16 below the plasma formation threshold makes it unsuitable for the present invention.

Due to complications arising from the need to cool an erbium laser medium at the higher pulse energy densities, and the need to compress pulses of an Nd:YLF laser medium at the lower pulse energy densities, it is preferred due to the purposes of the present invention to use both mediums and operate them in their respective regions of greatest efficacy. Specifically, it is preferred that an Nd:YLF laser medium be used to remove relatively large portions of corneal tissue in the first stage and that an erbium laser medium be used to smooth the corrected surface 38 by removing relatively small portions of corneal tissue therefrom. As for the actual generated characteristics of the respective beams it is preferred that the Nd:YLF laser be operated during the method's first stage in a regime wherein the resultant beam is pulsed to generate ten thousand pulses per second (10,000 pps) with each pulse having approximately one hundred micro joules (100 μJ) of energy (and being approximately thirty pico seconds (30 psec)) in duration. On the other hand, it is preferred that an erbium laser be operated during the method's second stage in a regime wherein the resultant beam is pulsed to generate two thousand pulses per second (2,000 pps) with each pulse having approximately five hundred micro joules (500 μJ) of energy and being approximately one hundred pico seconds (100 psec) in duration. As implied above, it is preferred that operation of the Nd:YLF laser during the first stage be accomplished at pulse energy densities generally at or above ten (10) J/cm² and that operation of the erbium laser during the second stage be accomplished at pulse energy densities generally below two (2) or three (3) J/cm².

It is to be appreciated that these particular regimes and ranges are only exemplary and that variations may be made therefrom without departing from the spirit and intent of the present invention.

While the particular method for reshaping the cornea as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as defined in the appended claims.

I claim:

1. A method for controlled reshaping of the cornea of the eye which comprises the steps of:
    removing a specified volume of corneal tissue by photoablation using laser pulses having plasma forming energy densities to establish a predetermined corrected surface; and
    smoothing said corrected surface by photoablation using laser pulses having energy densities substantially below an effective plasma forming level.

2. A method for controlled reshaping of the eye as recited in claim 1 wherein the laser has an energy and the energy of the laser used for said removing step is variable in a range greater than ten joules per square centimeter (I > 10 J/cm²).

3. A method for controlled reshaping of the eye as recited in claim 1 wherein the laser has an energy and the energy of the laser used for said smoothing step is variable in a range of 1–10 joules per square centimeter (1–10 J/cm²).

4. A method for controlled reshaping of the eye as recited in claim 1 wherein said plasma forming energy density is greater than approximately ten joules per square centimeter (10 J/cm²).

5. A method for controlled reshaping of the eye as recited in claim 1 wherein said smoothing is accomplished using laser pulses having energy densities in the range of two to four joules per square centimeter (2–4 J/cm²).

6. A method for controlled reshaping of the eye as recited in claim 1 wherein said removing step is accomplished using a laser spot size which is larger than a laser spot size used for said smoothing step.

7. A method for controlled reshaping of the eye as recited in claim 6 wherein the laser spot size for said removing step is approximately one hundred microns in diameter and the laser spot size for said smoothing step is approximately one micron in diameter.

8. A method for controlled reshaping of the eye as recited in claim 1 wherein said removing step comprises:
    removing a epithelium in said specified volume by photoablation;
    removing Bowman's membrane in said specified volume by photoablation; and
    removing a stroma in said specified volume by photoablation.

9. A method for controlled reshaping of the eye as recited in claim 8 wherein said step of removing the epithelium is accomplished using a shorter wavelength than is used for removing the stroma.

10. A method for controlled reshaping of the eye as recited in claim 9 wherein said wavelength for removing the epithelium is 0.527 microns.

11. A method for controlled reshaping of the eye as recited in claim 9 wherein said wavelength for removing the stroma is 2.94 microns.

12. A method for controlled reshaping of the eye as recited in claim 9 wherein said wavelength for removing the epithelium is 0.527 microns and the wavelength for removing the stroma is 2.94 microns.

13. A method for correcting vision which comprises the steps of:
determining a diopter correction necessary to achieve substantially normal vision;
calculating an extent of corneal tissue corresponding to said diopter correction;
removing a specified volume of corneal tissue from said eye by photoablation to reshape the eye in accordance with said calculated extent using laser pulses having plasma forming energy densities; and
smoothing said corrected surface by photoablation using laser pulses having energy densities substantially below an effective plasma forming level.

14. A method for correcting vision as recited in claim 13 wherein said calculating step is accomplished by equating a change of one diopter with a change of approximately eight microns of corneal tissue thickness along the visual axis of the eye.

15. A method for correcting vision as recited in claim 13 wherein said calculated extent is measured into the eye from surface thereof substantially along the visual axis of the eye and said volume of removed corneal tissue is contained between the surface of said eye and a plane substantially perpendicular to said visual axis at said calculated extent.

16. A method for correcting vision as recited in claim 13 wherein removing said volume of corneal tissue creates a corrected surface for the eye and comprises the steps of:
removing a epithelium in said specified volume by photoablation;
removing Bowman's membrane in said specified volume by photoablation; and
removing a stroma in said specified volume by photoablation.

17. A method for controlled reshaping of the eye as recited in claim 16 wherein said step of removing the epithelium is accomplished using a shorter wavelength than is used for removing the stroma.

18. A method for controlled reshaping of the eye as recited in claim 11 wherein said removing step is accomplished using a laser spot size which is larger than a laser spot size used for said smoothing step.

19. A method for controlled reshaping of the eye as recited in claim 18 wherein the laser spot size for said removing step is approximately one hundred microns in diameter and the laser spot size for said smoothing step is approximately one micron in diameter.

20. A method for reshaping the cornea of an eye for improved vision which comprises the steps of:
defining a specified volume of corneal tissue to be removed;
aiming a beam of laser pulses at said specified volume;
focusing said pulses to a predetermined spot size;
setting the power in said pulses above a plasma forming level to photoablate corneal tissue with each of said pulses to a depth of approximately eight (8) microns;
scanning said beam through said specified volume to photoablate and remove said corneal tissue therein and expose a corrected surface;
subsequently setting the power in said pulses effectively below said plasma forming level to photoablate corneal tissue with each of said pulses to a depth of approximately one (1) micron; and
scanning said beam across said corrected surface to photoablate and smooth corneal tissue at said corrected surface.

21. A method for reshaping the cornea of an eye for improved vision as recited in claim 20 wherein the diameter of said spot size is varied between approximately one hundred (100) microns and one (1) micron.

22. A method for reshaping the cornea of an eye for improved vision as recited in claim 20 by removing a epithelium in said specified volume by photoablation; removing Bowman's membrane in said specified volume by photoablation; and removing a stroma in said specified volume by photoablation.

23. A method for reshaping the cornea of an eye for improved vision as recited in claim 22 wherein said step of removing the epithelium is accomplished using a shorter wavelength than is used for removing the stroma.

24. A method for reshaping the cornea of an eye for improved vision as recited in claim 20 further comprising the steps of:
determining a diopter correction necessary to achieve substantially normal vision; and
calculating an extent of corneal tissue corresponding to said diopter correction and scanning said beam to reshape the eye by said calculated extent.

25. A method for reshaping the cornea of an eye for improved vision as recited in claim 24 wherein the power of said laser pulse used for reshaping the eye is variable in the range of one (1) to ten (10) joules per square centimeter (1–10 J/cm$^2$).

* * * * *